United States Patent [19]
Tolkoff et al.

[11] Patent Number: 5,743,891
[45] Date of Patent: Apr. 28, 1998

[54] SUBCUTANEOUS SAFETY CATHETER ASSEMBLY

[75] Inventors: M. Joshua Tolkoff, Brookline; Fernando Alvarez de Toledo, Concord, both of Mass.

[73] Assignee: ACT Medical, Inc., Newton, Mass.

[21] Appl. No.: 738,003

[22] Filed: Oct. 25, 1996

[51] Int. Cl.⁶ .................................................. A61M 25/00
[52] U.S. Cl. ........................ 604/282; 604/164; 604/192; 604/198; 604/280; 604/281
[58] Field of Search ............................. 604/19, 53, 66, 604/101, 264–270, 280–282, 192, 198

[56] References Cited

U.S. PATENT DOCUMENTS

| | | | |
|---|---|---|---|
| 4,368,730 | 1/1983 | Sharrock | 604/282 X |
| 4,571,241 | 2/1986 | Christopher | 604/282 X |
| 4,863,442 | 9/1989 | DeMello et al. | 604/282 |
| 5,125,909 | 6/1992 | Heimberger | 604/282 X |
| 5,180,376 | 1/1993 | Fischell | 604/282 |
| 5,607,407 | 3/1997 | Tolkoff et al. | 604/282 |

*Primary Examiner*—Sam Rimell
*Assistant Examiner*—Robert V. Racunas
*Attorney, Agent, or Firm*—Iandiorio & Teska

[57] ABSTRACT

A subcutaneous safety catheter assembly includes a flexible catheter having an inner wall including a hollow stiffening member which is stiff in the longitudinal direction and flexible laterally; a needle having a sharp point at one end and a grip at the other and being adapted to being disposed in the hollow stiffening member with the sharp point extending beyond the distal end of the member; and a needle guard at the proximal end of the member for securely engaging the needle and shielding the sharp point of the needle upon its withdrawal from the catheter.

9 Claims, 7 Drawing Sheets

SUBCUTANEOUS SAFETY CATHETER ASSEMBLY

FIELD OF INVENTION

This invention relates to a subcutaneous safety catheter assembly, and more particularly to such an assembly which includes a flexible catheter with rigidifying means and a needle guard.

BACKGROUND OF INVENTION

There are a number of problems associated with the use of conventional rigid hypodermic needles to introduce catheters to the human body either directly or through subcutaneous access ports. Hypodermic needles inserted in port septa are very uncomfortable for the patient, particularly for extended infusion regimes. In addition, the hypodermic needle tends to rock and move with body motion. This movement can result in the needle dislodging. If the needle partially dislodges, blood or infused liquid is pumped beneath the skin which can cause tissue damage and an increased risk of infection. Further, if the needle totally dislodges, the liquid could contaminate the surrounding area. Furthermore, needle movement can lead to severe septum damage and subsequent leakage. And tissue damage can result from the rigid nature of the hypodermic itself.

One attempt to alleviate these problems involves using "L"-shaped, right-angle needles. Unfortunately, the length of the needle arm from the tip to the elbow of the needle must vary from patient to patient—obese patients will require deep penetration, while thinner patients will require shallower penetration. Accordingly, healthcare facilities must keep a variety of right-angle needle sizes on hand to accommodate a variety of patient types. Furthermore, the correct right-angle needle size can only be determined by trial and error, often requiring several applications before the healthcare practitioner determines the optimal depth of penetration for a given patient. This practice is still further complicated by the fact that many patients who require infusion therapy often undergo dramatic changes in weight, thus requiring the healthcare practitioner to reevaluate the correct needle size with every visit.

Another shortcoming of rigid needles in general is that they require extensive dressing with gauze and tape or, in the alternative, require a very specialized and expensive infusion set to prevent the dislodging effect described above.

Some have attempted to develop more comfortable, flexible catheters for subcutaneous access ports. One example is a product which utilizes an elaborate needle inserting device to anchor and insert the flexible tube into the port described in U.S. Pat. No. 5,135,502 to Koenig, Jr. et al. This device is difficult to use and involves an expensive inserting device.

Patients who require frequent infusion therapy often opt to have a subcutaneous vascular access port surgically implanted. These ports generally contain a tough, self-sealing septum which is positioned just below the skin. The tough septum is permanently compressed and held in a rigid access port housing which is sutured directly to muscle tissue to prevent movement. The housing confines a sealed reservoir directly beneath the septum. The housing is typically made of titanium, stainless steel, DELRIN® acetal resin, polysulfone or some other biocompatible and drug compatible material. The reservoir communicates with a vein or artery by way of a silicone or polyurethane connector tube. Although most commercial subcutaneous access port systems share these common elements, a variety of different configurations have been proposed. For a further discussion of subcutaneous access port devices see: Foltz, *Evaluation of Implanted Infusion Devices*, NITA, Vol. 10, No. 1, pp. 49–51 (1987); Goodman et al., *Venous Access Devices—An Overview*, Oncol. Nurs. Forum, Vol. 11, No. 5, p. 16–23 (1984); and May et al., *Percutaneous Catheters and Totally Implanted Access Systems*, Journal of Intravenous Nursing, Vol 11, No 2, pp. 97–103 (1988), incorporated herein by reference.

In practice, a doctor or nurse palpates the skin to find the outer perimeter or rim of the implanted port septum and then inserts a rigid, metal hypodermic needle directly through the skin and through the septum until the bottom of the reservoir is reached. Infusion therapy is then initiated. When the needle is removed the septum self-seals.

The self-sealing septa used in these devices are very tough and typically from about 0.200 inch to about 0.500 inch thick. These septa are required to be tough enough to withstand thousands of punctures with a 19, 20, 21 or 22 gauge hypodermic needle and still maintain an effective seal.

Other subcutaneous medical devices utilizing this type of tough, self-sealing septa include hydrocephalus shunts, dialysis grafts and artificial organs, all of which require intermittent introduction and/or removal of fluid material. These septa are typically mounted in a port housing similar to the subcutaneous vascular access port described above.

More recently an approach has been suggested which utilizes a flexible catheter with a rigidifying means. A needle disposed in the catheter is used during installation to puncture the skin (and the port if there is one) and insert the catheter, after which the needle is withdrawn and discarded. The needle is sharp and presents a hazard to healthcare workers as well as the patient.

SUMMARY OF INVENTION

It is therefore an object of this invention to provide an improved subcutaneous safety catheter assembly.

It is a further object to provide such a subcutaneous safety catheter assembly which is rigid during insertion and flexible thereafter upon removal of the needle and provides a safety needle guard for the withdrawn needle.

It is a further object to provide such a subcutaneous safety catheter assembly which is relatively simple, inexpensive and highly effective.

It is a further object to provide such a subcutaneous safety catheter assembly which is comfortable for the patient, remains stable despite body motion, and is less apt to damage tissue.

It is a further object to provide such a subcutaneous safety catheter assembly which uses one size needle for all patients.

The invention results from the realization that a truly safe, stable, comfortable, simple and inexpensive subcutaneous safety catheter assembly can be effected with a flexible catheter housing, a provisional stiffening member which is rigid when a force is applied to it longitudinally using an elongate puncture needle in place in the catheter and becomes flexible after insertion into the patient and withdrawal of the needle whose tip is thereafter safely engaged and shielded by a needle guard.

This invention features a subcutaneous safety catheter assembly including a flexible catheter having an inner wall including a hollow stiffening member which is stiff in the longitudinal direction and flexible laterally and an outer wall including a sheath surrounding the member. There is a needle having a sharp point at one end and a grip at the other and adapted to being disposed in the hollow stiffening member with the sharp point extending beyond the distal end of the member. A needle guard at the proximal end of the member securely engages the needle and shields the sharp point of the needle upon its withdrawal from the catheter.

In a preferred embodiment the stiffening member may have an interrupted wall. The stiffening member may be a corrugated tube, a pleated tube, a braided tube or a tube having a plurality of longitudinally spaced semicircular gaps. The semicircular gaps may extend circumferentially perpendicular to the longitudinal axis of the tube.

DISCLOSURE OF PREFERRED EMBODIMENT

Other objects, features and advantages will occur to those skilled in the art from the following description of a preferred embodiment and the accompanying drawings, in which.

Figure 1:
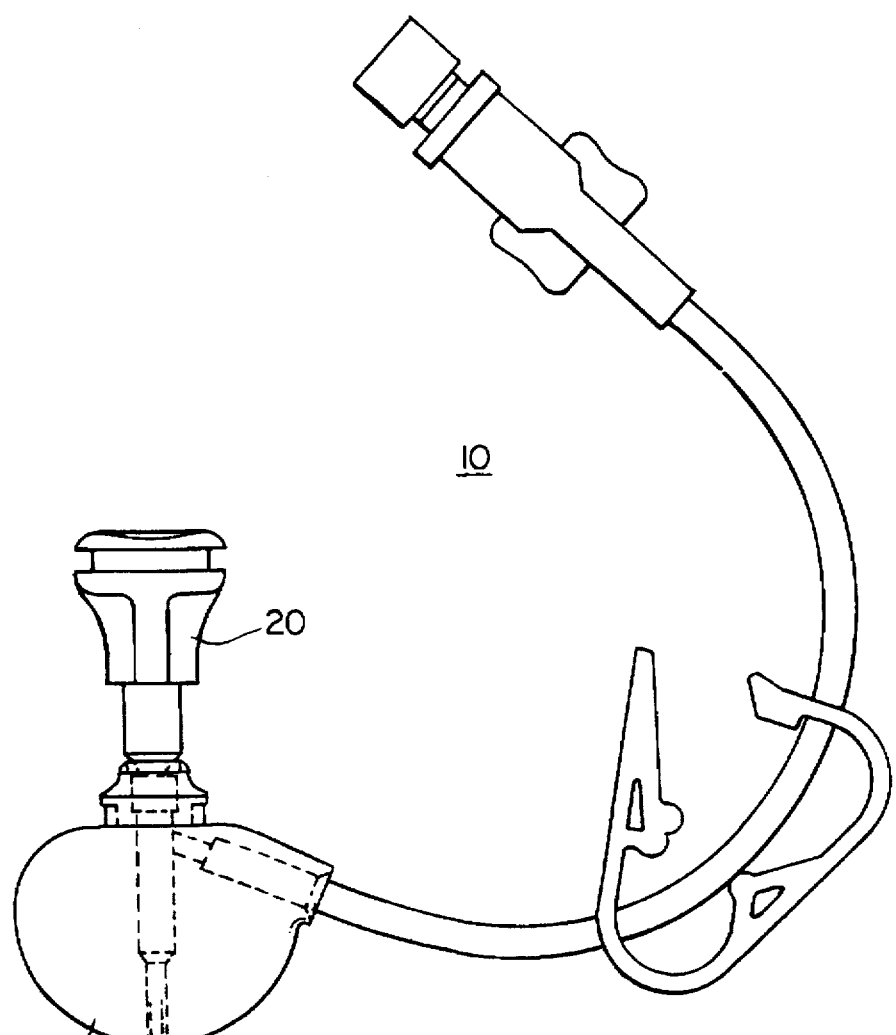
FIG. 1 is a front elevational view of a subcutaneous catheter assembly in accordance with the present invention.
Figure 1A:
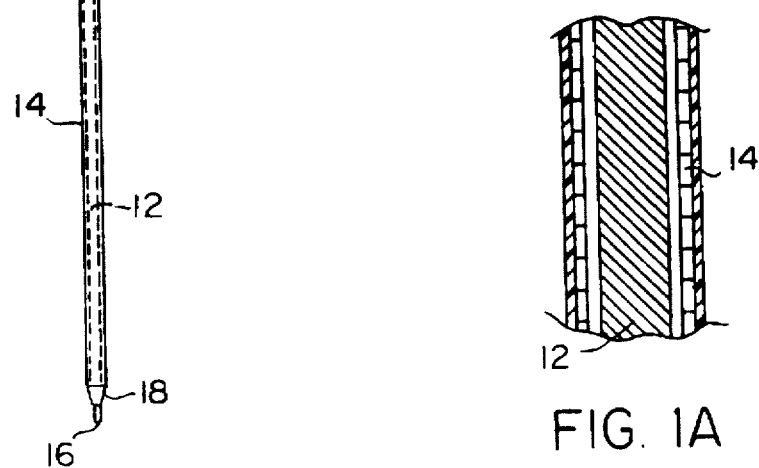
FIG. 1A is an enlarged view of portion of the assembly of FIG. 1.

There is shown in FIG. 1 a subcutaneous catheter assembly 10 according to this invention which includes an elongated needle 12 disposed coaxially within a flexible hollow stiffening member 14. Tip 16 at the distal end of needle 12 extends beyond the tip 18 of hollow member 14 when needle 12 is installed in member 14. A knob or grip 20 is mounted at the proximal end of needle 12 to aid introduction and withdrawal of the assembly 10 from the patient's vascular access port or flesh. At the proximal end of hollow member 14 is a hub 22 which facilitates connection of the catheter to an external source of intravenous fluid after the needle 12 is removed. Hub 22 can be any suitable connection means, preferably a luer lock connector.

Figure 2:
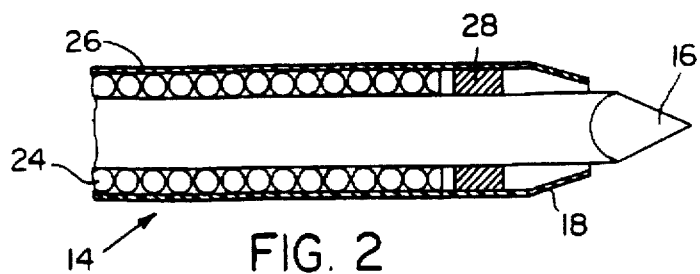
FIG. 2 is an enlarged detailed view of the tip of the catheter of FIG. 1 with the needle inserted in a coil made of round wire.
Figure 3:
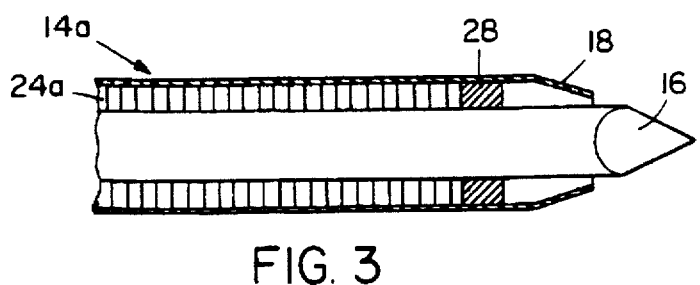
FIG. 3 is an enlarged detailed view of the tip of the catheter of FIG. 1 with the needle inserted in a coil made of ribbon wire.

As can be seen in greater detail in FIG. 2, hollow member 14 is formed of a helical coil made of round wire 24 covered by a supple plastic sheet 26. Bushing 28 may be provided to accommodate and guide the point or tip 16 of needle 12 through the catheter. Hollow member 14 is not limited to a helical coil made with round wire. For example, as shown in FIG. 3, hollow column member 14a can be formed of a flat ribbon wire 24a. Helical coil 24a is typically wound with its turns contacting each other. Typically the coil is characterized as a pretensioned coil which refers to coil which requires a pulling force to cause a separation between the individual coil turns.

A pre-tensioned coil is required for proper performance of the present catheter. Without it there is no stiffened column effect. Pre-tensioning of the coil improves the overall stiffness of the catheter assembly under compression. This would be the case when the catheter is being pushed through the tough septum of a vascular access port. This effect can be measured by the following procedure:

1. The catheter is clamped in a pin vise with 1.4 inches exposed.
2. The pin vise is then mounted on the force-arm of an Accu-Force "Cadet" force gauge manufactured by Ametek. The pin vise is oriented such that the catheter tip is perpendicular to the gauge. This enables the user to measure the force necessary to deflect the tip. As used herein, the term "resistive force" shall mean the force necessary to deflect the tip 0.300 inch (0.0762 cm).
3. As additional compressive forces are applied to the coil the force required to deflect the tip increases.

Pre-tensioned coils according to the present invention produce a significant increase in resistive force for the entire catheter assembly as compressive forces are increased. Resistive forces at 3 lb. compressive force are at least 5% greater than the resistive forces measured at 0 lb. compressive force (i.e., no load). Preferably, the resistive forces at 3 lb. compressive force are at least 25% greater than the resistive forces measured at 0 lb. compressive force. Most preferably, the resistive forces at 3 lb. compressive force are at lest 50% greater than the resistive forces measured at 0 lb. compressive force. This translates into a very stiff catheter assembly during the period when compressive forces are applied to push the catheter through the tough septum of a subcutaneous vascular access port. However, once compressive forces are no longer applied, the catheter assembly becomes more flexible. This provides the patient with a more comfortable infusion system. For example, a catheter according to the present invention fabricated from: a 0.030 inch inside diameter coil consisting of a 10 gauge stainless steel wire having a 2°–3° negative lead angle; a 0.028 inch outside diameter puncture needle; and a sheath formed from a Teflon tube having a wall thickness of 0.007 inch exhibits a resistive force at 3 lb. compressive force of about 0.24 lb. as compared with a resistive force measured at 0 lb. compressive force of about 0.18 lb.

Figure 4:
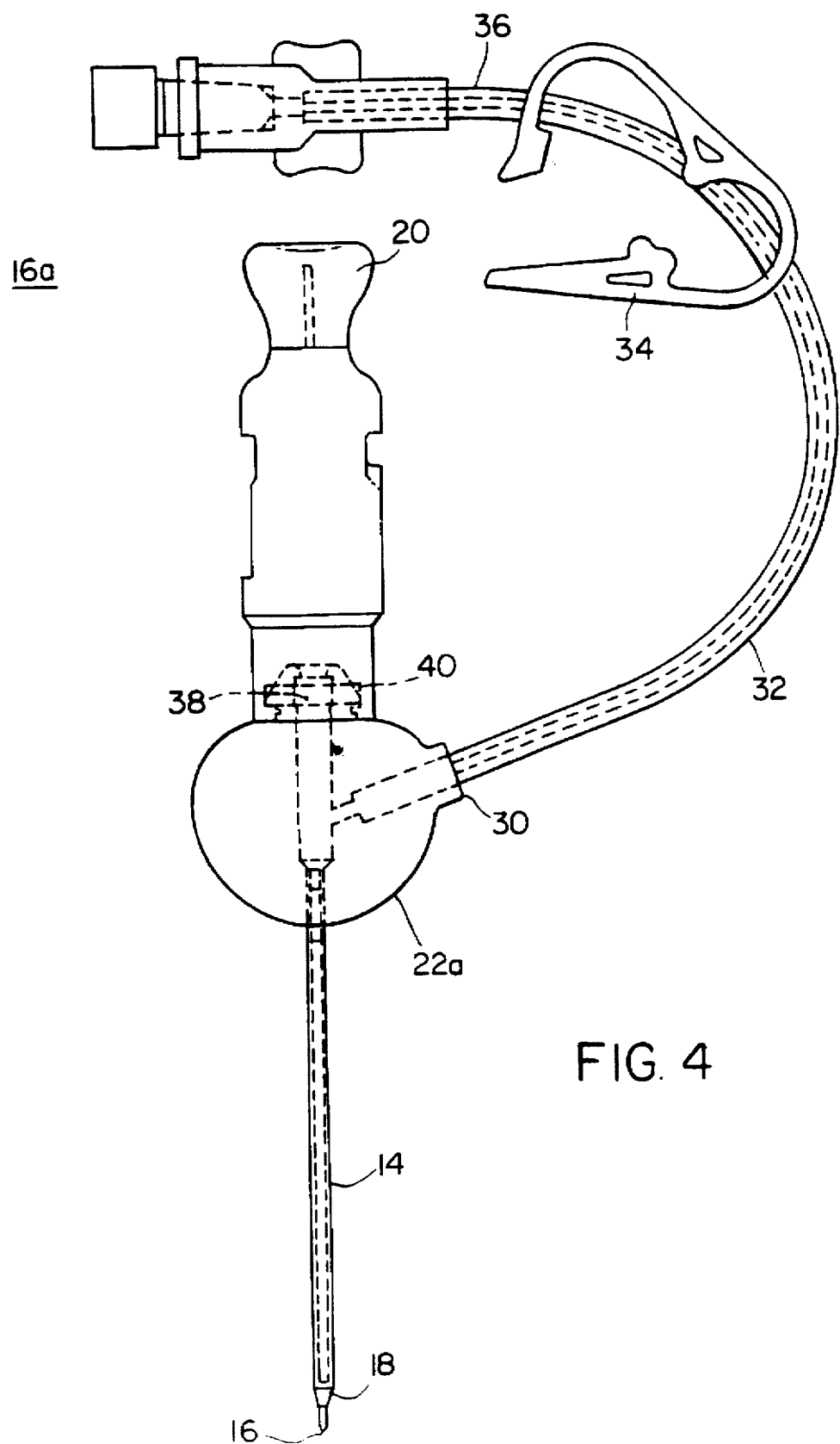
FIG. 4 is a view similar to FIG. 1 of a preferred subcutaneous access port catheter assembly in accordance with the present invention.

In another embodiment the subcutaneous safety catheter assembly 10a, FIG. 4, more suited for use in subcutaneous vascular access port infusion therapy, includes a hub 22a which has a port 30 that forms a Y junction for interconnection with tube 32, the flow through which is controlled by pinch clamp 34. The end 36 of tube 32 is connected to any suitable source of infusion therapy fluid.

In operation, the force on the knob 20 forces the sharp point 16 of needle 12 and along with it the tip 18 and the remainder of hollow member 14 through the patient's skin into the vascular access port. After insertion needle 12 is withdrawn by gripping knob or grip 20 and withdrawing it from the remainder of catheter 14. Once needle 12 is withdrawn from catheter 14 the remaining hollow member 14 including the helical coil 24 and sheath 26 becomes much more laterally flexible so that the catheter can be easily bent, arranged and comfortably affixed to the patient. Needle 12 may be solid to perform solely a puncture function or may be cannulated to convey fluid into the patient. A seal 38 is provided at aperture 40 of hub 22a to provide a seal against leakage of body fluids from the patient or infusion fluids from tube 32 after needle 12 has been withdrawn. Seal 38 may be formed from a membrane under compression similar to the construction of a vascular access port. The synergy between needle 12 and hollow member 14 is an important part of the functioning of the catheter assembly. A typical access port membrane under compression has a Shore hardness greater than 25 on the A scale and typically from 25 to 50. But neither the needle 12 nor member 14 has to have sufficient stiffness to penetrate such tough self-sealing septums. Rather, it is only the combination of the two, needle 12 and member 14, acting together that must provide that stiffness. This synergistic stiffness occurs because needle 12 locks the coils 28 of hollow member 14, preventing the coil from moving radially or laterally to provide a minimum total stiffness corresponding to about the stiffness of a standard 22 gauge stainless steel needle. Once the penetration needle is removed the coils become unlocked and function quite flexibly which adds greatly to the ease of installation and comfort for the patient.

Figure 5:
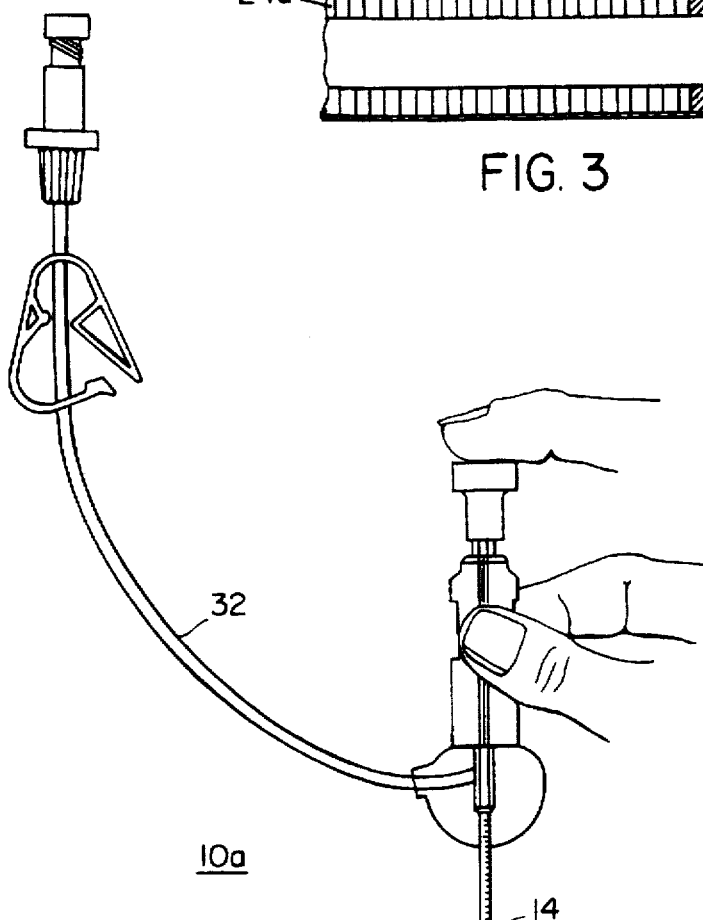
FIG. 5 depicts a manner in which the assembly of FIG. 4 may be inserted into a vascular access port.

A typical installation of catheter assembly 10a is shown in FIG. 5, where needle 12 (not visible) has already punctured the skin 50 of the patient and the septum 52 of the embedded access port 54 held in place by sutures 56 and 58. The fluid being fed from tube 32 through catheter assembly 10a is introduced through hollow member 14 into reservoir (not visible) in port 54 from whence it is fed out through coupling 59 in tube 60 to suitable locations in the patient's body.

Figure 6:
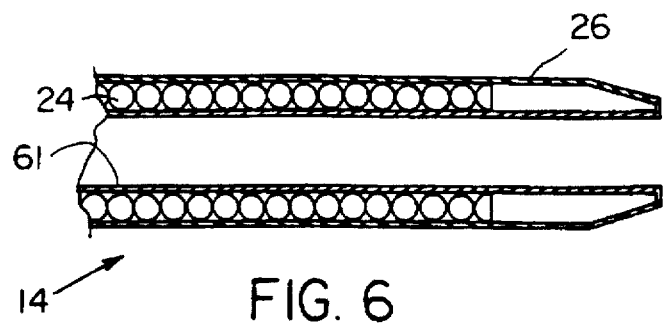
FIG. 6 is a longitudinal section of a helical coil similar to that of FIG. 2 with the addition of an inside sheath.
Figure 7:
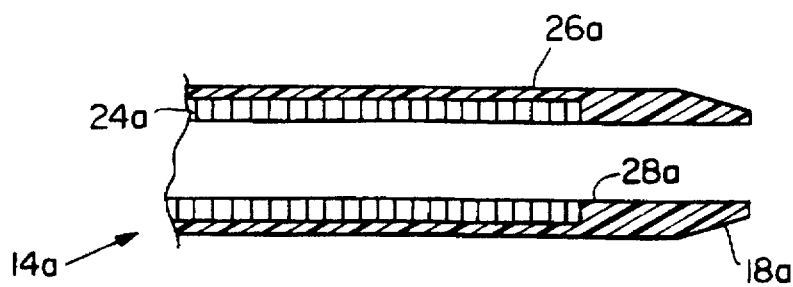
FIG. 7 is a longitudinal section of a helical coil similar to that of FIG. 6 but with a ribbon wire embedded in the sheath.

Hollow member 14 may include an inner sheath 61, FIG. 6, in addition to outer sheath 26. In addition, the hollow member may be formed with a coil such as exemplified by flat ribbon coil 14a, FIG. 7, wholly embedded in sheathing 26a, FIG. 7, and bushing 28a may be formed as an integral part of sheath 26a.

Figure 8:
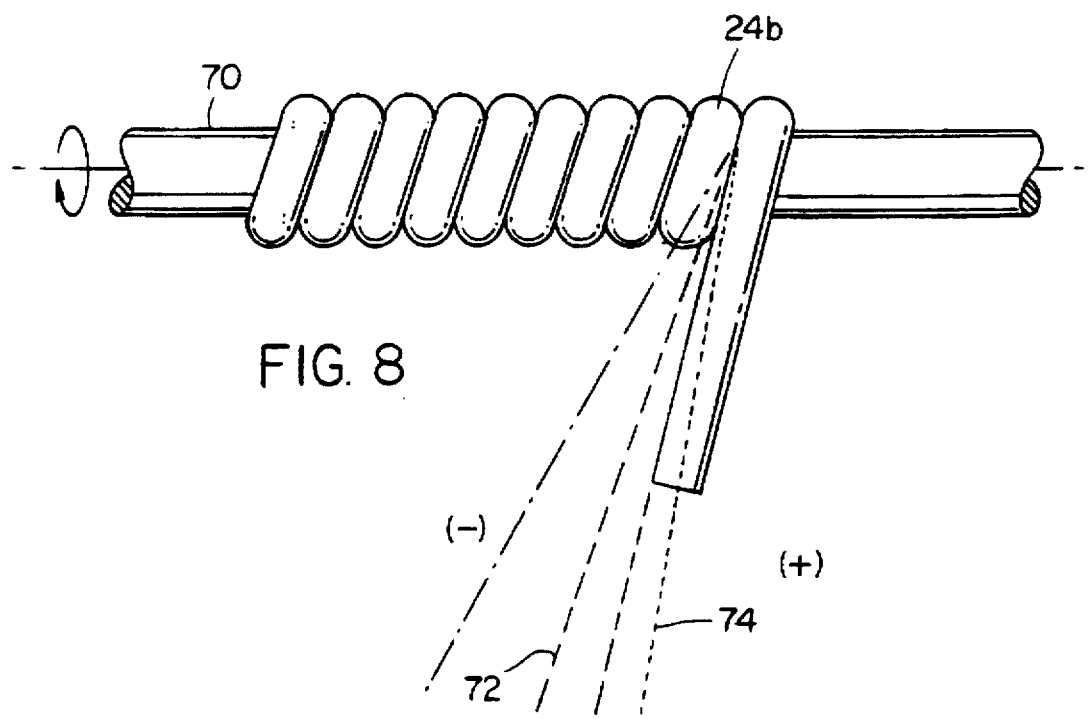
FIGS. 8 and 9 are schematic depictions of the wire-winding technique used to provide the pre-tensioned coils of the present invention.
Figure 9:
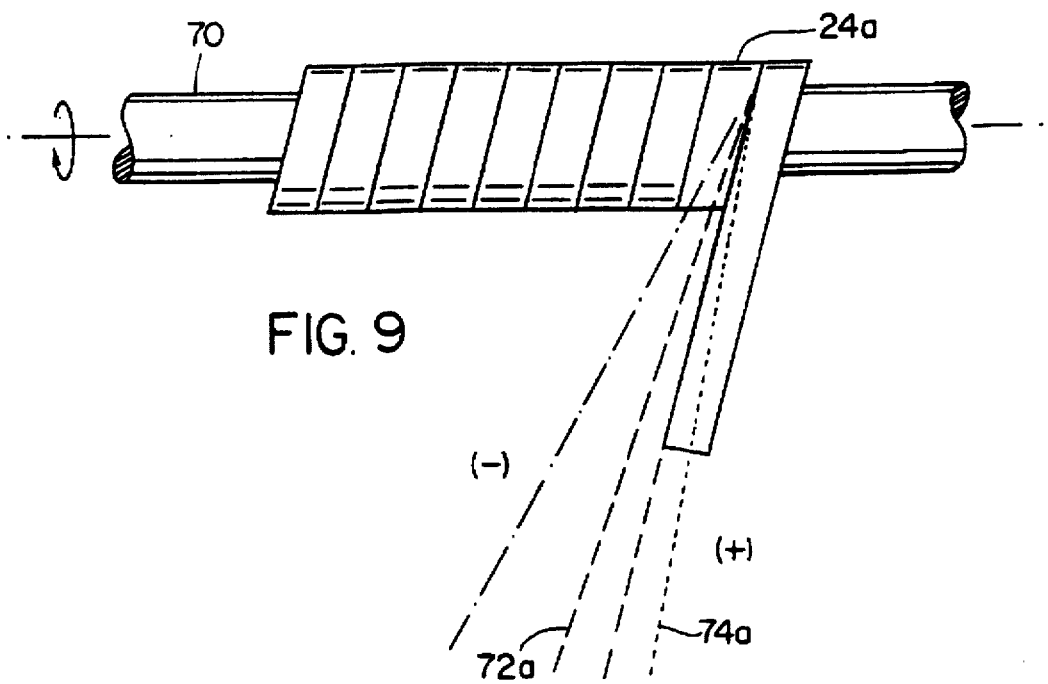

A pre-tensioned coil made of coil wire 24b, FIG. 8, can be made by a manual winding technique using a negative lead angle. Wire 24b which is shown round for illustrative purposes only—it may in fact be a flat ribbon wire such as 24a or any other suitable shape—is typically fixed to a rotating mandrel 70. As the helix shape develops with each rotation of mandrel 70 the wire is advanced at an angle equal to the lead angle so that a zero lead angle 72 is produced. If the wire is advanced ahead of the wrapped wire a positive lead angle 74 is achieved. This results in spaces between the coils as can be seen in FIG. 2 of U.S. Pat. No. 4,044,765 to Kline. These spaces produce a bunching of the outer tube sheath 26 when compressive forces are applied. Since large compressive forces are necessary to puncture the tough septa of a subcutaneous access port this type of bunching results in the fatal instability of the catheter which renders it ineffective. If the wire is advanced behind the wrapped wire a negative lead angle is achieved. Negative lead angle wrapping results in a pre-tensioned coil in accordance with the present invention. Pre-tensioned coils exhibit greatly improved penetration ability when used in the catheter of the present invention. Preferably the negative lead angle is from 0° to 4°, most preferably from 2°–3°. Care is taken to not use too severe a negative lead angle as it will result in a doubling over or overwrapping of the coil. FIG. 9 illustrates a similar technique applied to a flat ribbon wire 24a.

Figure 10:
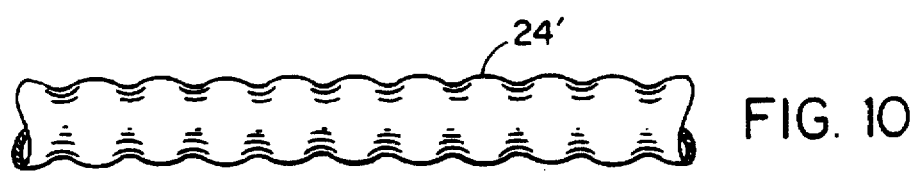
FIGS. 10, 11, 12 and 13 show four other forms of interrupted wall stiffening members in addition to a coil: corrugated, pleated, circumferentially gapped and braided, respectfully.
Figure 11:
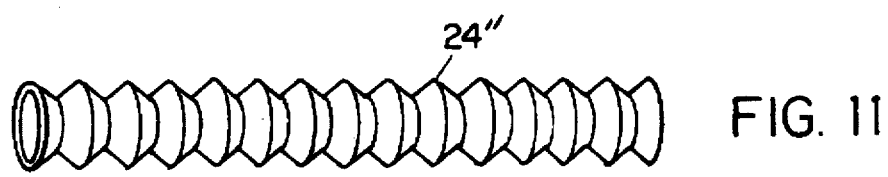
Figure 12:
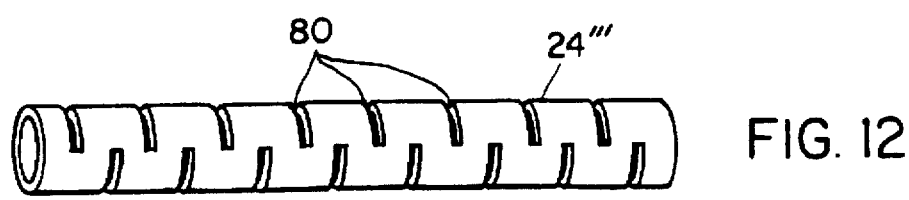
Figure 13:
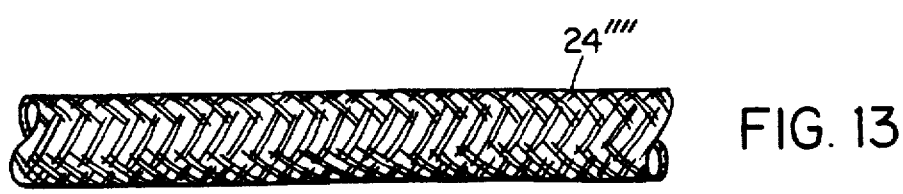

While thus far hollow member 14 has been shown constructed as a helix or coil using round, flat or other suitable wire, this is not a necessary limitation of the invention. What the invention contemplates is an elongated tubular member that has an interrupted surface such that stress relief is provided when the tube is bent so that the tube can be easily bent about its longitudinal axis. For example, coil wire 24 or 24a may be replaced by a tube 24', FIG. 10, which has an undulating surface that may be regular in the nature of corrugations or irregular. In another construction tube 24", FIG. 11, may be provided which has a pleated surface. Alternatively, tube 24'", FIG. 12, may be provided having semicircular longitudinally spaced gaps 80 which are preferably but not necessarily circumferentially disposed perpendicularly to the longitudinal axis of tube 24'". In yet another construction tube 24"" may be formed with a braiding process.

Figure 14:
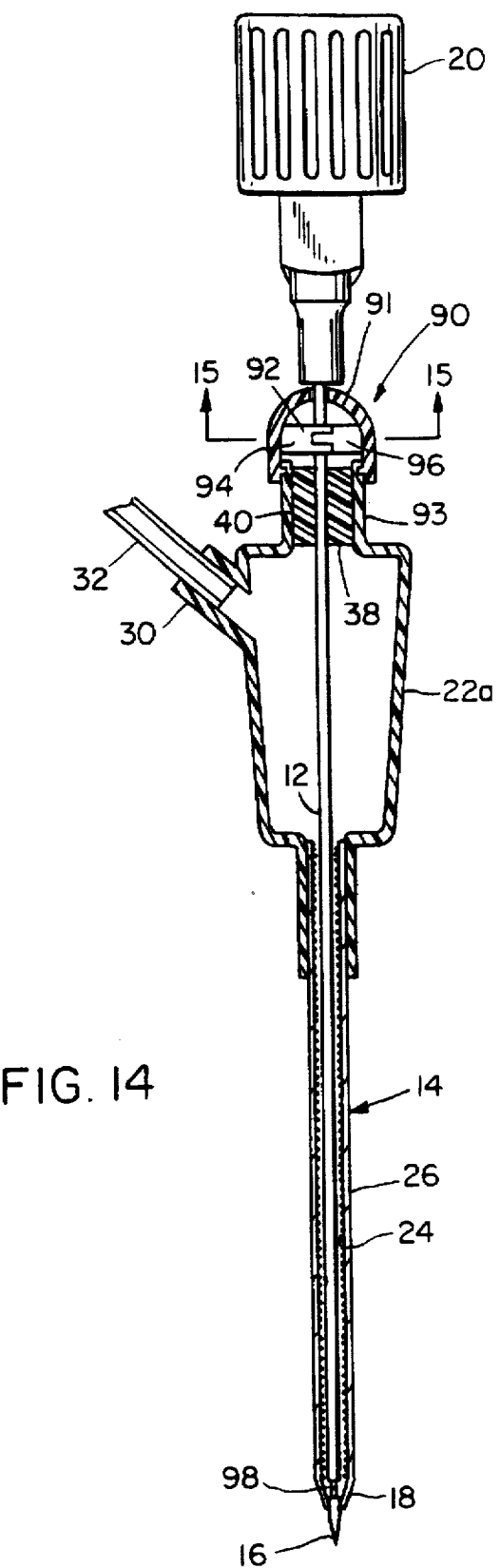
FIG. 14 is a side elevational sectional view of a subcutaneous catheter assembly with a needle guard according to this invention.
Figure 15:
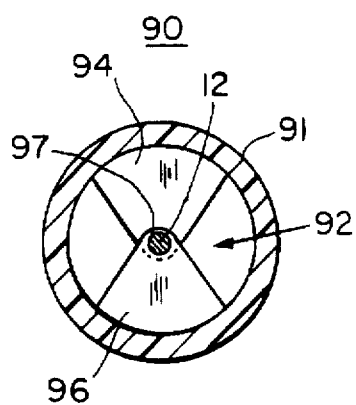
FIG. 15 is an enlarged detailed top plan sectional view of the double spring needle latch of FIG. 14 taken along lines 15—15.
Figure 16:
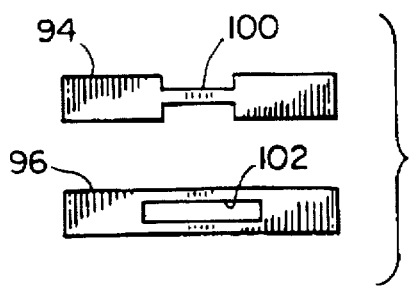
FIG. 16 is a further enlarged side elevational view of the two springs used in FIG. 15.
Figure 17:
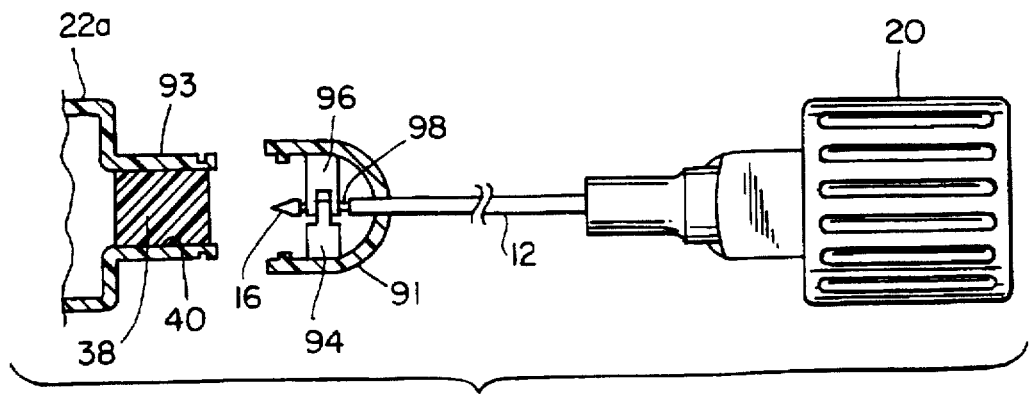
FIG. 17 is a partially broken away, side partially sectional view showing the needle latched with the needle guard of FIGS. 15 and 16.

Needle guard 90, FIG. 14, includes a shield 91 which is mounted to neck 93 of hub 22a and includes a latch 92 including two interlocking spring elements 94, 96 which snap over and grip the reduced section or notch 98 near the tip 16 of needle 12 when needle 12 is withdrawn from hollow member 14 through hub 22a and compression membrane or septum 38 through the use of knob or grip 20. The two elements 94 and 96 overlap, FIG. 15, to form gap 97 around needle 12. Element 94, FIG. 16, includes a reduced center section 100 which is narrow enough to fit into the elongated slot 102 of element 96. In this way the two interlock and overlap to normally accommodate the body of needle 12. However, when needle 12 is withdrawn, as shown in FIG. 17, and the reduced portion or notch 98 near point 16 of needle 12 moves through the capture space 97, the spring action of elements 94 and 96 tighten against the reduced section 98 so that the remaining normal sized portion of needle 12 near point 16 cannot be further withdrawn, thereby drawing shield 91 from neck 93 of hub 22a.

Figure 18:
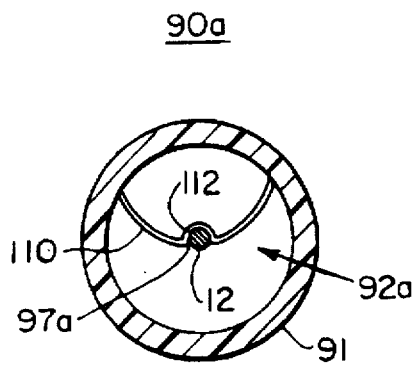
FIG. 18 is an enlarged detailed top plan sectional view of a single spring needle latch similar to that shown in FIG. 15.
Figure 19:
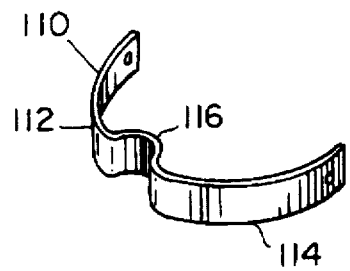
FIG. 19 is a further enlarged three-dimensional view of the single spring needle latch of FIG. 18.

In another construction needle guard 90a, FIG. 18, may include but one element 110 in latch 92a which provides a partial capture gap 112 that normally accommodates the body of needle 12 but extends when it encounters notch 98 to engage the reduced portion and lock the needle to shield 91. The construction of element 110 can be more easily discerned in FIG. 19 where the spring element is shown having a flat ribbon-like form similar to elements 94 and 96 with curved arms 112, 114 having a central section 116 of reverse curvature that provides the accommodation of needle 12 and the capture of notch 98.

Other suitable needle guards are disclosed in U.S. Pat. Nos. Re.344,416, Lemo, "IV Catheter With Self Locating Needle Guard", U.S. Patent Nos. 4,929,241; 5,458,658; 5,322,517; and 5,328,482. Further information regarding coils and coil winding is disclosed in U.S. Pat. No. 4,044,765 to Kline. Methods of coating the inside of a catheter with a fluorinated hydrocarbon are disclosed in U.S. Pat. No. 3,922,378 and 4,044,765 to Kline. Various intravenous catheters which use a coil guide mechanism are disclosed in U.S. Pat. Nos. 3,757,768; 3,841,308; 3,922,378; 4,044,765; 4,052,989; and 4,368,730, all of which are incorporated herein by reference.

The coil may be formed from stainless steel, platinum, tantalum, tungsten, NITINOL™ nickel/titanium alloy, rigid fibers or other similar medically approved material and an outer sheathing formed from a tube of smooth, inert flexible plastic material, such as TEFLON® fluorocarbon polymers, polyethylene, polypropylene, polyvinyl chloride or the equivalent thereof, that is heat-shrunk, mechanically-shrunk or a combination thereof over the coil in such a manner that the outer surface of the plastic tube remains smooth and its inner surface is formed into the spiral grooves on the outer surface of the coil, thus effecting a firm attachment between the sheathing tube and the coil; For a detailed discussion of a suitable type of heat shrink processing see U.S. Pat. No. 4,044,765 to Kline, incorporated herein by reference. Other methods of manufacture may also be used. For example, the surface of the coil could be dip-coated with suitable plastic, or the outer sheath could be injection molded, such that the interior of the molded tube would have a spiral contour which accepts the outer contour of the coil in the same way a nut accepts a screw thread.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A subcutaneous safety catheter assembly comprising:

a flexible catheter having an inner wall including a hollow stiffening member which is stiff in the longitudinal direction and flexible laterally;

a needle having a sharp point at one end and a grip at the other end adapted to being disposed in said hollow stiffening member with the sharp point extending beyond the distal end of said member; and needle guard means at the proximal end of said catheter for securely engaging said needle and shielding the sharp point of said needle automatically upon and after its withdrawal from said catheter.

2. The subcutaneous safety catheter assembly of claim 1 in which said stiffening member has an interrupted wall.

3. The subcutaneous safety catheter assembly of claim 2 in which said stiffening member is a corrugated tube.

4. The subcutaneous safety catheter assembly of claim 2 in which said stiffening member is a pleated tube.

5. The subcutaneous safety catheter assembly of claim 2 in which said stiffening member is a braided tube.

6. The subcutaneous safety catheter assembly of claim 2 in which said stiffening member is a tube having a plurality of longitudinally spaced semi-circular gaps.

7. The subcutaneous safety catheter assembly of claim 6 in which said gaps extend circumferentially, perpendicular to the longitudinal axis of said tube.

8. The subcutaneous safety catheter assembly of claim 6 in which said flexible catheter includes an outer wall including a sheath surrounding said member.

9. The assembly of claim 1 in which said needle guard means includes means for irremovably locking the guard about the needle upon and after its withdrawal from the catheter.

* * * * *